US011370766B2

United States Patent
Wang et al.

(10) Patent No.: US 11,370,766 B2
(45) Date of Patent: Jun. 28, 2022

(54) SULFONYL AMIDINE AS INDOLEAMINE-2,3-DIOXYGENASE INHIBITOR, AND PREPARATION METHOD THEREFOR AND USE THEREOF

(71) Applicant: SHANGHAI LONGWOOD BIOPHARMACEUTICALS CO., LTD., Shanghai (CN)

(72) Inventors: Zhe Wang, Shanghai (CN); Zhihong Zeng, Shanghai (CN)

(73) Assignee: SHANGHAI LONGWOOD BIOPHARMACEUTICALS CO., LTD., Shanghai (CN)

( * ) Notice: Subject to any disclaimer, the term of this patent is extended or adjusted under 35 U.S.C. 154(b) by 0 days.

(21) Appl. No.: 16/472,077

(22) PCT Filed: Dec. 22, 2017

(86) PCT No.: PCT/CN2017/117861
§ 371 (c)(1),
(2) Date: Jun. 20, 2019

(87) PCT Pub. No.: WO2018/113758
PCT Pub. Date: Jun. 28, 2018

(65) Prior Publication Data
US 2020/0207728 A1 Jul. 2, 2020

(30) Foreign Application Priority Data
Dec. 22, 2016 (CN) .......................... 201611201033.8

(51) Int. Cl.
  A61K 31/4245 (2006.01)
  C07D 271/04 (2006.01)
  A61P 35/04 (2006.01)
  A61K 45/06 (2006.01)
(52) U.S. Cl.
  CPC ............ C07D 271/04 (2013.01); A61P 35/04 (2018.01); *A61K 45/06* (2013.01)
(58) Field of Classification Search
  CPC .... A61K 31/4245; C07D 271/04; A61P 35/04
  USPC .......................................... 514/364; 548/125
  See application file for complete search history.

(56) References Cited

U.S. PATENT DOCUMENTS

2010/0015178 A1    1/2010   Combs et al.

FOREIGN PATENT DOCUMENTS

| CN | 102164902 A | 8/2011 | | |
|---|---|---|---|---|
| CN | 106565696 A | 4/2017 | | |
| WO | 2014/066834 A1 | 5/2014 | | |
| WO | 2015/119944 A1 | 8/2015 | | |
| WO | 2017/106062 A1 | 6/2017 | | |
| WO | 2017/143874 A1 | 8/2017 | | |
| WO | WO-2018072697 A1 | * 4/2018 | ......... | A61K 31/4245 |
| WO | WO-2018095432 A1 | * 5/2018 | ......... | A61K 31/4245 |

OTHER PUBLICATIONS

English translation of the claims of WO-2018072697-A1. (Year: 2018).*
English translation of the description of WO-2018072697-A1. (Year: 2018).*
English Translation of the International Search Report dated Feb. 24, 2018 corresponding to PCT/CN2017/117861 filed Dec. 22, 2017; 3 pages.

* cited by examiner

*Primary Examiner* — Joseph R Kosack
*Assistant Examiner* — Sagar Patel
(74) *Attorney, Agent, or Firm* — Mintz, Levin, Cohn, Ferris, Glovsky and Popeo, P.C.

(57) ABSTRACT

Provided in the present application are a sulfonyl amidine as represented by formula (I) as an indoleamine-2,3-dioxygenase inhibitor, and a preparation method therefor and the use thereof. The compound of formula (I) in the present application can be used as an indoleamine-2,3-dioxygenase inhibitor in the preparation of a drug for preventing and/or treating indoleamine-2,3-dioxygenase-mediated diseases.

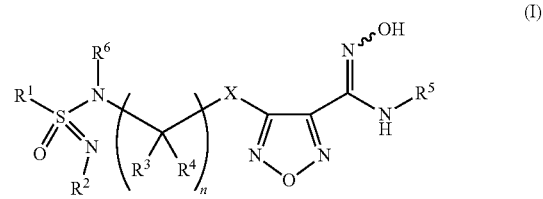

15 Claims, 1 Drawing Sheet

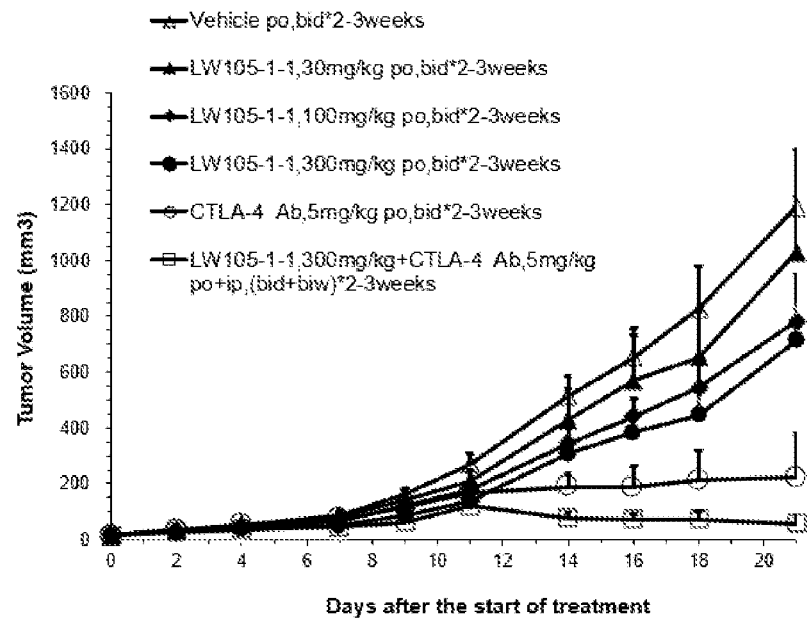
1A
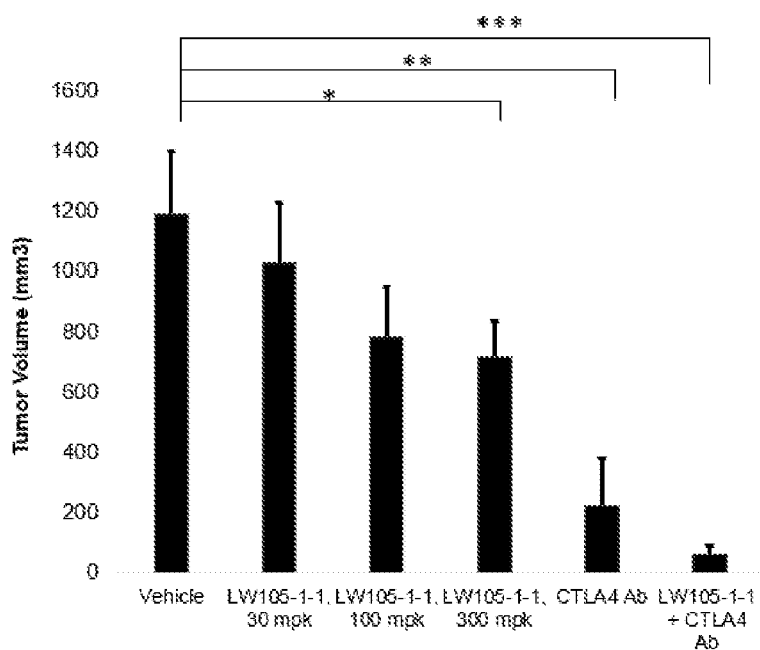
1B

SULFONYL AMIDINE AS INDOLEAMINE-2,3-DIOXYGENASE INHIBITOR, AND PREPARATION METHOD THEREFOR AND USE THEREOF

FIELD OF THE INVENTION

The present application relates to a sulfonyl amidine as indoleamine-2,3-dioxygenase inhibitor, a preparation method and use thereof, and more particularly to an indoleamine-2,3-dioxygenase inhibitor of which the structure containing a sulfonyl amidine and a 1,2,5-oxadiazole, and the preparation and use thereof.

BACKGROUND OF THE INVENTION

Indoleamine-2,3-dioxygenase (IDO) is a monomeric enzyme containing ferroheme found in the cell for the first time in 1967 by the Hayaishi et al, of which the cDNA encoding protein is composed by 403 amino acid, and the molecular weight thereof is 45 kDa. It is a rate-limiting enzyme which is catabolized along the tryptophan-kynurenine pathway and is widely expressed in many mammalian tissues (Hayaishi O. et al. Science, 1969, 164, 389-396). In tumor cells, IDO often plays an important physiological role in inducing tumor microenvironmental immune tolerance, and the tryptophan (Trp)-kynurenine (Kyn) metabolic pathway mediated by IDO is involved in tumor immune escape, and IDO also plays an important role in inducing tumor microenvironment immune tolerance.

Tryptophan is one of the important essential amino acids in mammals and needs to be taken in large quantities from food to maintain cell activation and proliferation, as well as the synthesis of proteins and some neurotransmitters. Therefore, lack of tryptophan would lead to dysfunction of some important cells. IDO can catalyze the conversion of tryptophan to N-formyl kynurenine in vivo, degrading the content of tryptophan and causing deficiency of tryptophan in vivo, leading to tumor formation. Immunohistological studies have shown that the kynurenine pathway can lead to an increase in the excitotoxic quinolinic acid, as well as many serious human diseases such as neurological diseases, e.g., Alzheimer's disease (Guillemin G. J. et al Neuropathol. And Appl. Neurobiol. 2005, 31, 395).

There are two main types of tryptophan rate-limiting enzymes in mammals: tryptophan dioxygenase (TDO) and IDO. In 1937, Kotake et al. purified proteins from rabbit intestines and found that TDO was mainly expressed in mammalian liver. It has not been found to be closely related to the immune system. TDO catalyzes the kynurenine pathway and converts tryptophan to N-formyl kynurenine [Higuchi K. et al J. Biochem. 1937, 25, 71-77; Shimizu T. et al J. Biol. Chem. 1978, 253, 4700-4706]. In 1978, the enzyme purified from the intestinal tract of rabbits was identified as a dioxygenase (IDO) containing heme, which is the only enzyme outside the liver that catalyzes the oxidative cleavage of indole in the tryptophan molecule to produce kynurenine and other metabolites. IDO is usually expressed in organs with more mucosa, such as lung, small intestine, large intestine, rectum, spleen, kidney, stomach and brain, and is widely distributed (Hayaishi O. et al, Proceedings of the tenth FEBS meeting, 1975, 131). Under certain special or pathological conditions, such as pregnancy, chronic infection, organ transplantation and tumors, IDO expression will increase significantly, and participate in mediating local immunosuppression.

Studies have shown that IDO can inhibit local T cell immune responses in the tumor microenvironment by: tryptophan depletion, toxic metabolism, and induction of regulatory T cell proliferation. In many cases, it overexpresses in tumors, thereby consuming local tryptophan and producing a large amount of metabolites such as kynurenine. In fact, in culture conditions in which tryptophan or kynurenine are absent, T cells would undergo proliferation inhibition, decreased activity, and even apoptosis. In T cells, there is a regulatory point that is very sensitive to the level of tryptophan. Under the action of IDO, tryptophan can be consumed, which leads to the arrest of T cells in the middle phase of G1, thereby inhibiting the proliferation of T cells as well as the immune response of T cells. Once T cells stop proliferating, they may not be stimulated any more. This is the mechanism of IDO immunity in vivo (Mellor A. et al Biochem. Biophys. Res. Commun. 2005, 338(1): 20-24) (LeRond S. et al J. Exp. Med. 2002, 196(4): 447-457). Currently, there is a need to develop new IDO inhibitors.

SUMMARY OF THE INVENTION

The object of the present application is to provide a novel compound containing sulfonyl amidine and 1,2,5-oxadiazole structure as a highly potent IDO inhibitor.

Another object of the present application is to provide a process for the preparation of such compound. Such compounds are not easy to synthesiz, and an effective method for preparing such compounds has been developed by the inventors' efforts.

In the first aspect of the present application, the application provides a compound of formula (I), or a pharmaceutically acceptable salt thereof, a deuterated compound, a stereoisomer or a tautomer thereof:

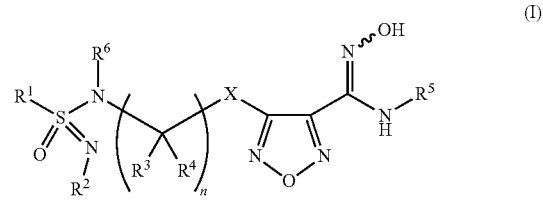

wherein, $R^1$ is substituted or unsubstituted $C_1$-$C_{10}$ alkyl, substituted or unsubstituted $C_3$-$C_{10}$ cycloalkyl, substituted or unsubstituted $C_2$-$C_{10}$ alkenyl, substituted or unsubstituted $C_3$-$C_{10}$ alkynyl, substituted or unsubstituted $C_6$-$C_{20}$ aryl, or substituted or unsubstituted $C_3$-$C_{14}$ heteroaryl; $R^2$, $R^3$, $R^4$ and $R^6$ are each independently hydrogen, substituted or unsubstituted $C_1$-$C_{10}$ alkyl, substituted or unsubstituted $C_3$-$C_{10}$ cycloalkyl, substituted or unsubstituted $C_2$-$C_{10}$ alkenyl, substituted or unsubstituted $C_3$-$C_{10}$ alkynyl, substituted or unsubstituted $C_6$-$C_{20}$ aryl, or substituted or unsubstituted $C_3$-$C_{14}$ heteroaryl; $R^1$ and $R^2$, $R^1$ and $R^3$, $R^1$ and $R^6$, $R^2$ and $R^6$, $R^3$ and $R^4$ or $R^3$ and $R^6$ may form a three to eight membered carbocyclic ring or a three to eight membered heterocyclic ring, wherein the hetero atom may be sulfur, oxygen, NH or $NR^f$;

$R^5$ is $C_6$-$C_{20}$ aryl, 5- or 6-membered heteroaryl; $R^5$ may be substituted by one or more groups selected from the group consisting of halogen, $C_1$-$C_6$ alkyl, $C_1$-$C_6$ alkoxy, hydroxyl, amino, nitro, aldehyde, —$CF_3$, —CN, —$SF_5$, $NR^aR^b$, carboxyl, —$COR^a$, —$CO_2C_1$-$C_6$ alkyl, —$CONR^aR^b$, —S(O)$R^a$, —S(O)$_2R^a$, —S(O)(NH)$R^a$, —S(O)(NR$^d$)$R^a$, —S(O)₂NRᵃRᵇ, —P(O)Me₂, —P(O)(OMe)₂; wherein each Rᵃ and each Rᵇ are independently hydrogen, substituted or unsubstituted C₁-C₁₀ alkyl, substituted or unsubstituted C₃-C₁₀ cycloalkyl, substituted or unsubstituted C₂-C₁₀ alkenyl, substituted or unsubstituted C₆-C₂₀ aryl, or substituted or unsubstituted C₃-C₁₄ heteroaryl; Rᵃ and Rᵇ may together form a three to eight membered ring or a four to eight membered heterocyclic ring, wherein the hetero atom may be sulfur, oxygen, NH or NRᶠ;

X is a single bond, O, S, NH or NRᵈ;

Rᵈ and Rᶠ are independently C₁-C₁₀ alkyl, C₃-C₁₀ cycloalkyl, C₆-C₂₀ aryl, or C₃-C₁₄ heteroaryl;

n is an integer from 2 to 8.

In some embodiments, "substituted" as used herein, unless otherwise specifically defined, refers to having one or more substituents selected from the group consisting of halogen, hydroxy, —NH₂, nitro, —CN, C₁-C₄ alkyl, C₁-C₄ haloalkyl, C₁-C₄ alkoxy, C₃-C₆ cycloalkyl, C₂-C₄ chain alkenyl, C₂-C₄ alkynyl, phenyl, benzyl.

In some embodiments, X is NH.

In some embodiments, R³ and R⁴ are each independently hydrogen, substituted or unsubstituted C₁-C₁₀ alkyl; R³ and R⁴ may together form a three to eight membered ring or a three to eight membered heterocyclic ring, wherein the hetero atom may be sulfur, oxygen, NH or NRᶠ.

In some embodiments, n is an integer from 2 to 6.

In some embodiments, R³ is hydrogen.

In some embodiments, R⁴ is hydrogen.

In some embodiments, the compound is as shown in formula (II),

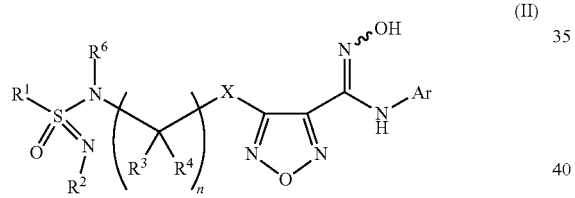

(II)

wherein,

Ar is benzene ring, and Ar may be substituted by one or more groups selected from the group consisting of halogen, C₁-C₆ alkyl, C₁-C₆ alkoxy, hydroxy, amino, nitro, aldehyde, —CF₃, —CN, —SF₃, —SF₅, NRᵃRᵇ, carboxyl group, —CORᵃ, —CO₂C₁-C₆ alkyl, —CONRᵃRᵇ, —S(O)Rᵃ, —S(O)₂Rᵃ, —S(O)(NH)Rᵃ, —S(O)(NRᵈ)Rᵃ, —S(O)₂NRᵃRᵇ;

wherein X, Rᵃ, Rᵇ, Rᵈ, R³, R⁴, R⁶, R², R¹ are as defined above; the hydrogen atom in the alkyl group may be substituted by halogen; n is an integer from 2 to 6.

In some embodiments, R¹ is C₁-C₁₀ alkyl, C₃-C₁₀ cycloalkyl, C₆-C₂₀ aryl, or C₃-C₁₀ heteroaryl; R¹ can be substituted by one or more halogens.

In some embodiments, R¹ is C₁-C₁₀ alkyl; R² and R⁶ are hydrogen, or C₁-C₁₀ alkyl; R³ and R⁴ are each independently hydrogen, or C₁-C₁₀ alkyl.

In some embodiments, R¹ selected from the group consisting of —CH₃, —C₂H₅, —CH(CH₃)₂, cyclopropane, CH₂F, CHF₂, CF₃, CH₂Cl, CHCl₂, CCl₃, CHFCH₃, CF₂CH₃, CHFCH₂F, CF₂CH₂F, CHFCHF₂, CF₂CHF₂, CHFCF₃ or CF₂CF₃.

In some embodiments, Ar is a benzene ring, the para position is substituted by F, and the meta position is substituted by Br.

In some embodiments, the compound is selected from the group consisting of:

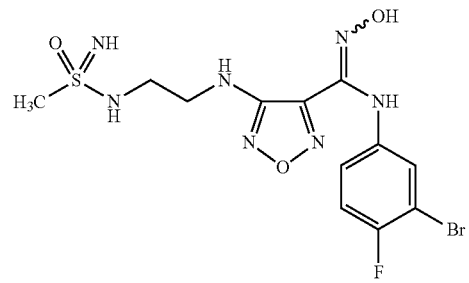

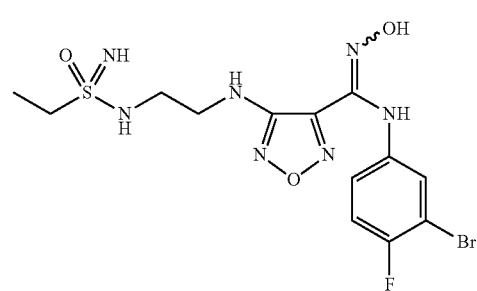

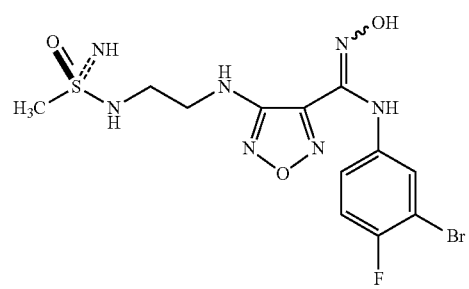

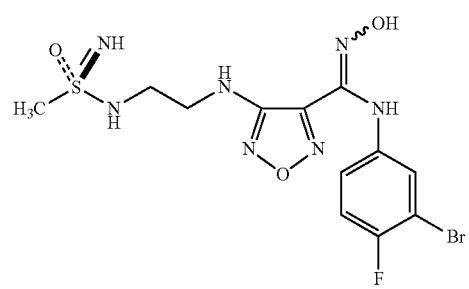

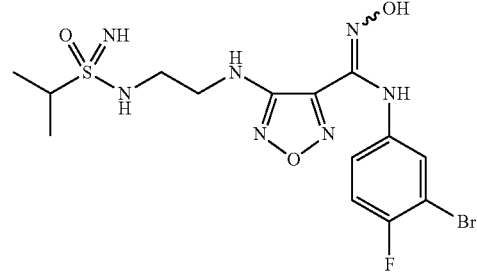

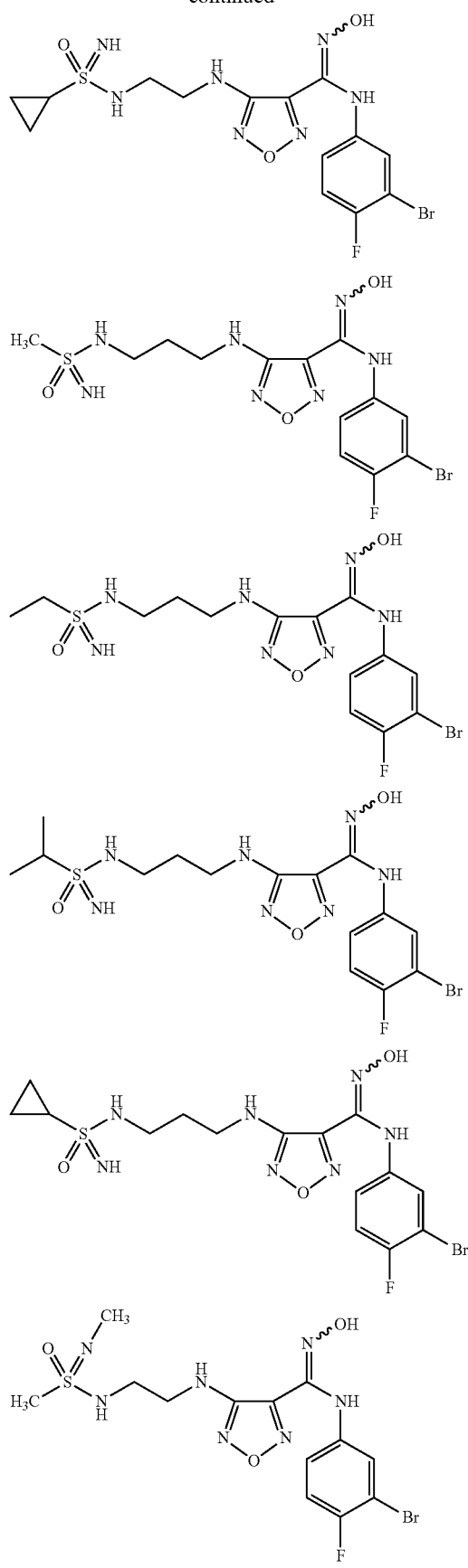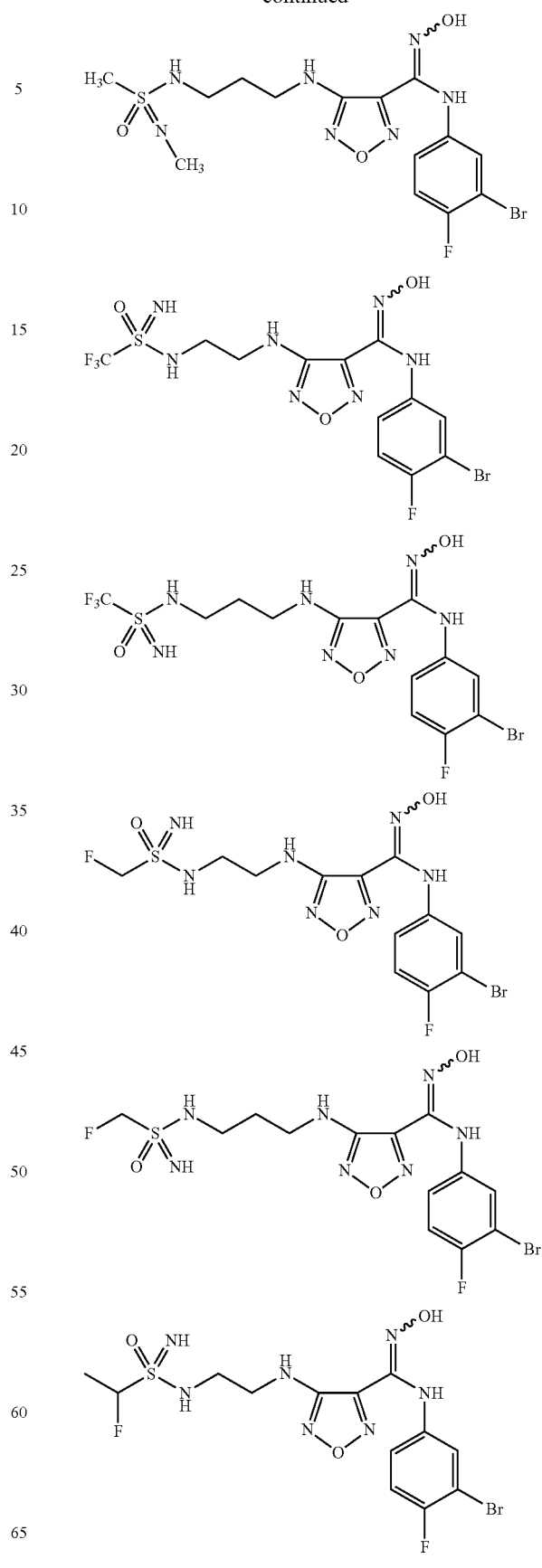

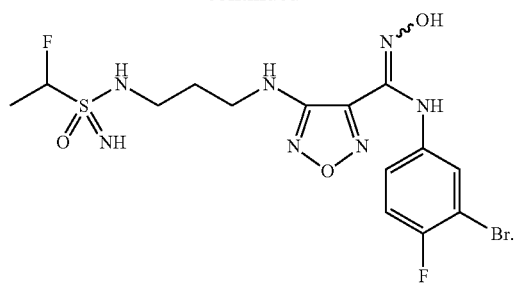

In the second aspect of the present application, a method of preparing the compound of the present invention is provided, comprising the steps:

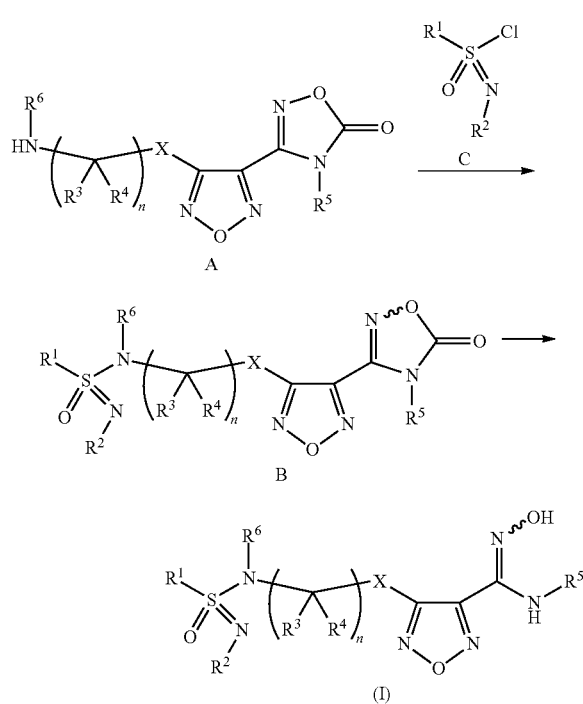

(a) reacting compound A with compound C to give compound B;

(b) ring-opening compound B under alkaline hydrolysis conditions (such as aqueous sodium hydroxide) to give the final product of formula I; In various formulas, $R^1$, $R^2$, $R^3$, $R^4$, $R^5$, $R^6$, n are as defined above.

The present application also provided a second preparation method comprising the following steps:

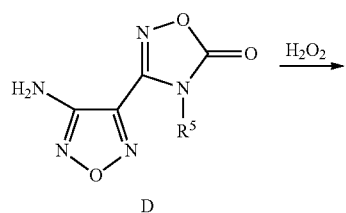

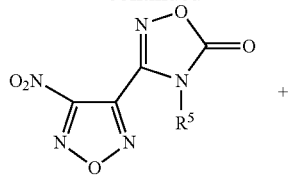

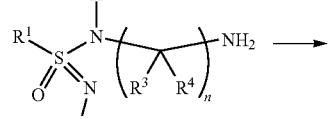

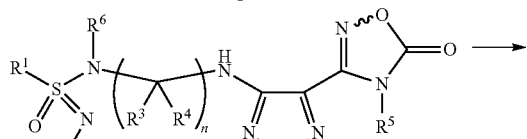

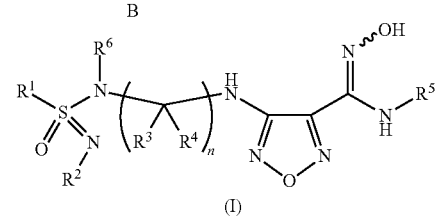

(a) under the catalysis of sulfuric acid, oxidizing compound D by hydrogen peroxide to provide compound E;

(b) compound E and compound F undergo a substitution reaction to obtain compound B;

(c) ring-opening compound B under alkaline hydrolysis conditions (such as aqueous sodium hydroxide) to give the final product of formula I.

In the third aspect of the present invention, a pharmaceutical composition is provided, wherein comprising: a compound of the present invention or a pharmaceutically acceptable salt thereof, a deuterated compound thereof, a stereoisomer thereof or a tautomer thereof; and a pharmaceutically acceptable carrier.

In the fourth aspect of the present invention, a pharmaceutical composition is provided, wherein comprising: a compound of the present invention or a pharmaceutically acceptable salt thereof, a deuterated compound thereof, a stereoisomer thereof or a tautomer thereof; and antitumor medicines. The anti-tumor drug and the compound described herein may be present in one dosage form or may be present separately in separate dosage forms.

In the fifth aspect of the present application, a compound of the present invention or a pharmaceutical composition thereof for use in the prevention and/or treatment of indoleamine-2,3-dioxygenase mediated diseases. The present application also provides the use of the compound or a pharmaceutical composition thereof for the preparation of a medicament for the prevention and/or treatment of a indoleamine-2,3-dioxygenase mediated disease. The present application further provides a method of preventing and/or treating a indoleamine-2,3-dioxygenase mediated disease comprising the step: administering to a patient in need thereof a therapeutically effective amount of a compound described herein, or the pharmaceutical composition described herein. The present application also provides the use of a compound of the present application, or a pharmaceutically acceptable salt thereof, a deuterated compound, a stereoisomer or a tautomer thereof, in the preparation of pharmaceutical compositions for treating cancer, eye diseases, heart disorders, depression, anxiety, and Alzheimer's disease and/or autoimmune diseases.

In some embodiments, the indoleamine-2,3-dioxygenase mediated diseases described herein are diseases characterized by the pathology of an IDO-mediated tryptophan metabolism pathway.

In some embodiments, the indoleamine-2,3-dioxygenase-mediated disease described herein is selected from the group consisting of cancer, eye disease, psychological disorders, depression, anxiety, Alzheimer's disease, and/or autoimmune disease.

In some embodiments, the cancers described herein include, but are not limited to, colorectal cancer, breast cancer, gastric cancer, lung cancer, colon cancer, pancreatic cancer, ovarian cancer, prostate cancer, renal cancer, liver cancer, brain cancer, melanoma, multiple myeloma, chronic myeloid leukemia, hematological tumors, including metastatic lesions in other tissues or organs away from the primary site of the tumor.

In some embodiments, when the disease being treated is cancer, the compound of the present application, or a pharmaceutically acceptable salt thereof, a deuterated compound, a stereoisomer thereof, or a tautomer thereof, may be administrated in combination with additional anti-cancer agent (also known as an anti-tumor drug). When used in combination, two or more active ingredients may be formulated into one dosage form, or different active ingredients may be separately prepared into separate dosage forms.

In some embodiments, the anti-tumor drug includes, but is not limited to, an immunotherapeutic drug for cancer: PD-1 antibody, CTLA-4 antibody, PD-L1 antibody, PD-L2 antibody, and any other chemotherapeutic drug or targeting medicine.

DESCRIPTION OF THE DRAWINGS

FIG. 1 shows the tumor growth inhibition effect of the compound LW105-1-1 of the present application in a mouse primary colorectal cancer tumor CT-26 model, wherein 1A is a curve graph and 1B is a histogram.

EMBODIMENTS FOR CARRYING OUT THE INVENTION

Unless otherwise defined, all technical and scientific terms used herein have the same meaning as commonly understood by one of ordinary skill in the art to which this application belongs. As used herein, when used in reference to a particular recited value, the term "about" means the value can vary by no more than 1% from the recited value.

Definition of Terms

The term "alkyl" refers to a monovalent saturated aliphatic hydrocarbon group having from 1 to 10 carbon atoms, including straight-chain and branched hydrocarbon groups such as methyl (ie, $CH_3$—), ethyl (ie, $CH_3CH_2$—), n-propyl. (i.e. $CH_3CH_2CH_2$—), isopropyl (i.e., $(CH_3)_2CH$—), n-butyl (i.e. $CH_3CH_2CH_2CH_2$—), isobutyl (i.e., $(CH_3)_2CHCH_2$—), sec-butyl (i.e., $(CH_3)(CH_3CH_2)CH$—), t-butyl (i.e., $(CH_3)_3C$—), n-pentyl (i.e. $CH_3CH_2CH_2CH_2CH_2$—), neo-pentyl (i.e., $(CH_3)_3CCH_2$—). In the present application, the term includes substituted or unsubstituted alkyl groups.

As used herein, the term "substituted or unsubstituted", "optionally substitute" or "optionally substituted" means that the group may be unsubstituted or substituted.

The term "substitute", "substituted" or "substitution" means that the group has one or more (preferably 1 to 6, more preferably 1 to 3) substituents selected from the group consisting of the following groups: halogen, hydroxy, —$NH_2$, nitro, —CN, $C_1$-$C_4$ alkyl, $C_1$-$C_4$ haloalkyl, $C_1$-$C_4$ alkoxy, $C_3$-$C_6$ cycloalkyl, $C_2$-$C_4$ alkenyl, $C_2$-$C_4$ alkynyl, phenyl, benzyl.

As used herein, the term "cycloalkyl" refers to a substituted or unsubstituted $C_3$-$C_{12}$ cycloalkyl group, such as $C_3$-$C_6$ cycloalkyl.

As used herein, the term "alkoxy" refers to —O-alkyl, wherein the alkyl group can be saturated or unsaturated, and can be branched, straight chain, or cyclic. Preferably, the alkoxy group comprises 1 to 10 carbon atoms, preferably 1 to 6 carbon atoms. Representative examples include, but are not limited to, methoxy, ethoxy, propoxy.

As used herein, the term "aryl" refers to an aromatic carbocyclic group of 6 to 20 (eg, 6-14, 6-10) carbon atoms which has a single ring (eg, phenyl) or a fused ring (such as naphthyl or anthracenyl), and if the point of attachment is on an aromatic carbon atom, the fused ring can be non-aromatic (eg 2-benzoxazolone, 2H-1,4-benzoxazin-3(4H)-one-7-yl, etc). Preferred aryl groups include phenyl and naphthyl. The term includes substituted or unsubstituted forms wherein the substituents are as defined above.

The term "alkenyl" as used herein refers to an alkenyl having 2 to 10 (eg, 2 to 6, or 2 to 4) carbon atoms and having at least 1 (eg, 1 to 2) unsaturated ethylenic bonds (>C=C<). Examples of such groups are vinyl, allyl, but-3-enyl. As used herein, the term "cycloalkyl" refers to a cyclic alkyl group having from 3 to 10 carbon atoms having single or multiple ring (including fused systems, bridged ring systems, and spiro ring systems). In a fused ring system, one or more of the rings may be a cycloalkyl, heterocyclic, aryl or heteroaryl group as long as the attachment site is via the ring of the cycloalkyl group. Examples of suitable cycloalkyl groups include, for example, adamantyl, cyclopropyl, cyclobutyl, cyclopentyl and cyclooctyl.

As used herein, the term "halo" or "halogen" refers to fluoro, chloro, bromo and iodo.

As used herein, the term "heteroaryl" refers to an aromatic group having from 1 to 10 carbon atoms and from 1 to 4 heteroatoms selected from the group consisting of oxygen, nitrogen and sulfur in the ring, such heteroaryl groups may be monocyclic (such as pyridyl or furyl) or fused (such as benzothienyl), wherein the fused ring may be non-aromatic and/or containing one hetero atom as long as the attachment site is via an aromatic heteroaryl atom. In one embodiment, the ring atom nitrogen and/or sulfur of the heteroaryl group is optionally oxidized to an N-oxide (N—O), a sulfinyl group or a sulfonyl group. Preferred heteroaryl groups include pyridinyl, pyrrolyl, indolyl, thienyl and furanyl. The term includes substituted or unsubstituted heteroaryl. The substituted heteroaryl group means a heteroaryl group substituted by 1 to 5, preferably 1 to 3, more preferably 1 to 2 substituents selected from the same substituent as defined for the substituted aryl group.

As used herein, the term "heterocycle" or "heterocyclic" or "heterocycloalkyl" or "heterocyclyl" refers to a saturated, partially saturated or unsaturated group (but not aromatic), having a single ring or a fused ring (including bridged ring system and spiro ring system having from 1 to 10 carbon atoms and from 1 to 4 heteroatoms selected from nitrogen, sulfur or oxygen in the ring, in a fused ring system, one or more rings may be cycloalkyl, aryl or heteroaryl group, as long as the attachment site is via an non-aromatic ring. In some embodiments, the nitrogen and/or sulfur atom of the heterocyclic group is optionally oxidized to provide an N-oxide, sulfinyl, or sulfonyl moiety. The "substituted heterocyclic ring" or "substituted heterocycloalkyl" or "substituted heterocyclic group" means a heterocyclic group substituted with 1 to 5 (e.g., 1 to 3) substituents, wherein the substituent is as defined above.

As used herein, the term "stereoisomer" refers to compounds which are chirally different in one or more stereocenters. Stereoisomers include enantiomers and diastereomers.

As used herein, the term "tautomer" refers to an alternative form of a compound having a different proton position, such as an enol-ketone, an imine-enamine, and an amide-imidic tautomer, or heteroaryl group tautomeric forms, wherein the heteroaryl group comprises a ring atom attaching to the —NH— moiety of the ring or the =N— moiety of the ring, such as pyrazole, imidazole, benzimidazole, triazole and tetrazole.

The compounds of the present application also include various geometric isomers. The bond represented by the wavy line "  " means that the structure represents a cis isomer or trans isomer, or a mixture of cis and trans isomers in any ratio.

As used herein, the term "compound of the present application" refers to a compound of formula (I), formula (II), or refers to the compound of formula (I), (II), the deuterated compound, racemate, stereoisomer or tautomer thereof, or a pharmaceutically acceptable salt thereof. The present application relates to racemic mixtures of these compounds, mixtures in which any of the enantiomers is enriched, and any of the isolated enantiomers.

When there are existing stereoisomers of any compound described herein, the present application includes all stereoisomers of the compound.

When there is existing tautomer of any compound described herein, the present application includes all tautomers of the compound.

The present application also encompasses deuterated compounds produced by the replacement of any one or more of the hydrogen atoms of the compound by its stable isotope deuterium.

Unless otherwise stated, in compounds of the present application, each chiral carbon atom (chiral center) may optionally be in R configuration or S configuration, or the mixture of R configuration and S configuration.

The pharmaceutical compositions described herein comprise the active ingredient in a safe and effective amount, and pharmaceutically acceptable carriers.

As used herein, "active ingredient" refers to a compound described in the present application, or a pharmaceutically acceptable salt thereof, a deuterated compound, a stereoisomer thereof, or a tautomer thereof. The "active ingredient" and pharmaceutical compositions described in the present application can be used as IDO inhibitors. The "safe and effective dosage" means that the amount of active ingredients is sufficient to significantly ameliorate the condition without causing serious side effects. In general, the pharmaceutical compositions contain from 1 to 2000 mg of active ingredient, for example, from 10 to 200 mg of active ingredient.

"Pharmaceutically acceptable" means the substance is suitable for use in tissues with humans and animals without undue toxicity, irritation, allergic reactions or other problems or complications.

The salt in "pharmaceutically acceptable salt" refers to an acid addition salt or a base addition salt formed by the compound of the present application, for example, an acid addition salt formed with an inorganic or organic acid, or base addition salt formed with an inorganic or organic base.

"Pharmaceutically acceptable carrier" means one or more compatible solid or liquid fillers, or gelatinous materials which are suitable for human use and should be of sufficient purity and sufficiently low toxicity. Each component of the pharmaceutical composition should be compatible with the active ingredient. "Compatibility" means that the components such as carriers in the composition can be admixed with the compounds of the present application and with each other without significantly reducing the efficacy of the active ingredient.

The compounds of the present application can be administered as separate active agents, or in combination with one or more other agents useful for treating cancer (i.e., antitumor drugs). The compounds of the present application can be administered concurrently with radiation therapy.

In general, the compounds of the present application are administered in a therapeutically effective amount, the actual amount of which is determined by a number of factors, such as the severity of the condition to be treated, the age and relative health of the patient, the potency of the compound being used, the route and form of administration, and other factors. The drug can be administered multiple times a day, such as once or twice a day. All of these factors are within the consideration of the attending physician. The therapeutically effective dose can generally be a total daily dose for a single or divided administration to a patient, for example, from about 0.001 to about 1000 mg/kg body weight per day, specifically, such as from about 1.0 to about 30 mg/kg body weight per day. In general, the compounds of the present application can be administered as a pharmaceutical composition by any of the following routes: oral, systemic (e.g., transdermal, intranasal or by suppository), or parenteral (e.g., intramuscular, intravenous or subcutaneous). The compositions may take the form of tablets, pills, capsules, semi-solids, powders, sustained release formulations, solutions, suspensions, elixirs, aerosols, or any other suitable compositions.

Suitable pharmaceutically acceptable carriers or excipients or salts are described in Remington's Pharmaceutical Sciences, Mack Pub. Co., New Jersey (1991).

The present application will be further illustrated below with reference to the specific examples. It should be understood that these examples are only to illustrate the application but not to limit the scope of the application. The experimental methods with no specific conditions described in the following examples are generally performed under the conventional conditions such as J. Sambrook et al., Molecular Cloning: A Laboratory Manual (New York: Cold Spring Harbor Laboratory Press, 1989), or according to the manufacturer's instructions.

Unless otherwise defined, the technical terms and scientific terminology used herein are of the same meanings as with that familiar to all to those skilled in the art. In addition, any methods and materials similar or equal to that recorded can be applied in the method described in the present application. The embodiments and the materials described herein are for demonstration purposes only.

Example 1

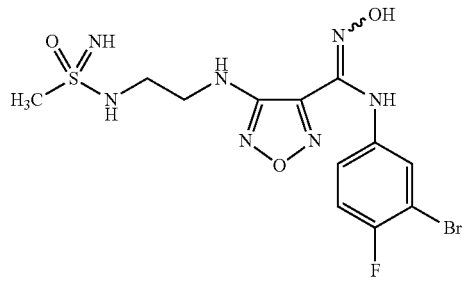

Step 1: Synthesis of N-(tert-butyldimethylsilyl)methylsulfonamide

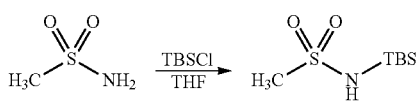

Under a nitrogen atmosphere, methanesulfonamide (9.50 g) was dissolved in THF (150 ml), triethylamine (20.24 g) was added at room temperature, and solution of TBSCl (17.33 g) in toluene (50 ml) was added dropwise. The reaction was carried out at room temperature for 18 hours. After the mixture was filtered, the residue was washed with diethyl ether (200 ml), and then diethyl ether (100 ml) was added to the filtrate. The mixture was allowed to stand for 30 min, and then filtered again. The filtrate was concentrated to give a solid, and n-heptane (300 ml) was added there into. The mixture was stirred at room temperature for 1 hour and filtered, and the solid was vacuum dried at room temperature to give 15.13 g product, yield 72.3%.

Step 2: Synthesis of N-(tert-butyldimethylsilyl)methylsulfone decanoyl chloride

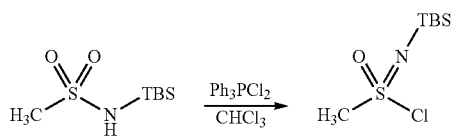

Under a nitrogen atmosphere, triphenylphosphine (2.89 g) and hexachloroethane (2.60 g) were added to chloroform (30 ml) and heated to 70° C. to react for 6 hours. A large amount of white solid was produced, and the reaction was cooled to 0-5° C. Triethylamine (1.52 g) was added, stirred for 10 min, then N-(tert-butyldimethylsilyl)methylsulfonamide (2.09 g) in chloroform (10 ml) was added. The mixture was stirred under 0-5° C. for 20 min to give 0.25 M solution of N-(tert-butyldimethylsilyl)methylsulfone decanoyl chloride. The solution was used directly in the next step.

Step 3: synthesis of N-(2-benzyloxycarbonylamino)ethyl-N'-tert-butyldimethylsilyl-methylsulfone oxime

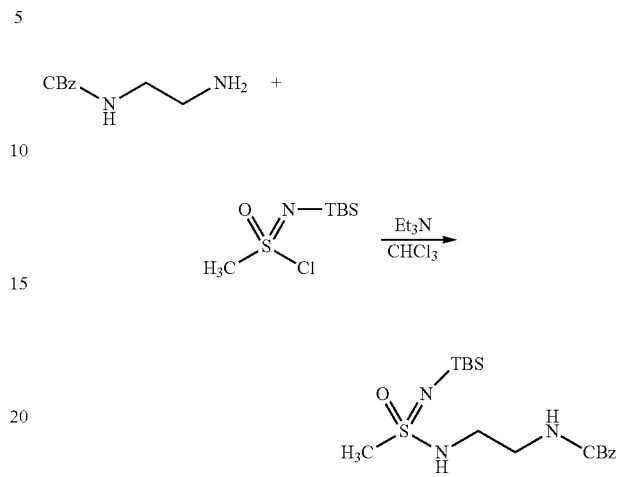

Under a nitrogen atmosphere, the solution of N-(tert-butyldimethylsilyl)methylsulfonyl decanoyl chloride (0.25 M, 40 ml) was cooled to 0-5° C., and mono CBz ethylenediamine (1.94 g) in chloroform (10 ml) was added. After the addition was completed, the reaction was warmed to room temperature and reacted for 1 hour, then directly separated by column chromatography to obtain a product 610 mg of N-(2-benzyloxycarbonylamino)ethyl-N'-tert-butyldimethylsilyl-methylsulfone oxime (containing phenoxyphosphine).

Step 4: synthesis of N-aminoethyl-N'-tert-butyldimethylsilyl-methylsulfone oxime

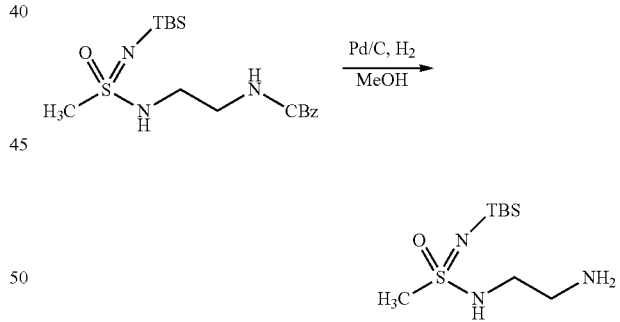

N-(2-benzyloxycarbonylamino)ethyl-N-carbonyl-tert-butyldimethylsilyl-methylsulfone oxime (610 mg) was dissolved in methanol (10 ml), and replaced with nitrogen for three times. Pd/C 10% (comprising 58% of water, 125 mg) was added, after replaced with hydrogen, the mixture was stirred at room temperature for 4 hours, and TLC tracking shown that the starting material has been consumed. After filtration, the mixture was concentrated and column chromatography separated to give 119 mg of N-aminoethyl-N'-tert-butyldimethylsilyl-methylsulfone oxime.

$^1$HNMR (400 MHz, CDCl$_3$): 3.13 (m, 2H), 2.95 (s, 3H), 2.88 (t, 2H, J=6.0 Hz), 1.75 (br, 3H), 0.90 (s, 9H), 0.11 (s, 3H), 0.10 (s, 3H).

Step 5: Synthesis of 4-(3-bromo-4-fluorophenyl)-3-(4-nitro-1,2,5-oxadiazol)yl-1,2,4-oxadiazol-5(4H)-one

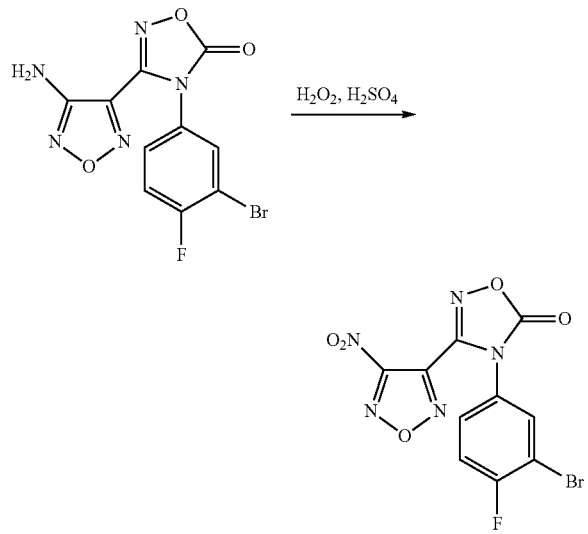

Sodium tungstate (1.0 g) was added into 35% hydrogen peroxide (25 ml), cool to 0-5° C., and concentrated sulfuric acid (25 ml) was added and stir for 10 min. 4-(3-Bromo-4-fluorophenyl)-3-(4-amino-1,2,5-oxadiazol)yl-1,2,4-oxadiazol-5(4H)-one (1.0 g) was added in one time, and reacted for 2 days at room temperature. The reaction solution was poured into ice water (200 g), and sodium carbonate solid was added, and the pH was adjusted to 8-9, then extracted with DCM. After concentration, the mixture was column chromatography purified (mobile phase was n-heptane/ethyl acetate=3:1) to provide white solid 0.80 g, yield 74%.

$^1$HNMR (400 MHz, d6-DMSO): 8.02 (dd, 1H, J=2.4, 6.0 Hz), 7.64 (m, 1H), 7.54 (t, 1H, J=8.4 Hz).

Step 6: 4-(3-bromo-4-fluorophenyl)-3-(4-(2-(N'-tert-butyldimethylsilyl-methylsulfonylamino)ethyl)amino-1,2,5-oxadiazol)yl-1,2,4-oxadiazol-5(4H)-one

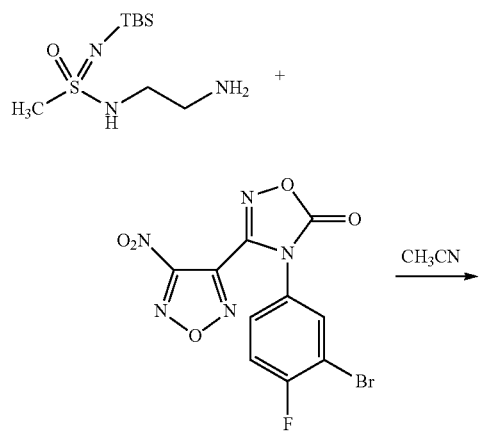

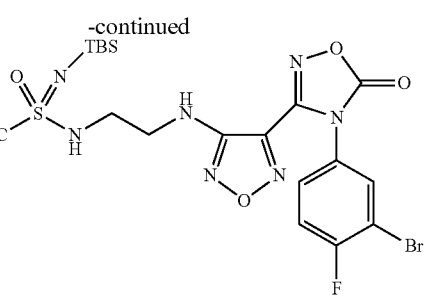

N-aminoethyl-N-tert-butyldimethylsilyl-methylsulfone oxime (110 mg) was dissolved in acetonitrile (2 ml), cooled to 0-5° C., then 4-(3-bromo-4-fluorophenyl)-3-(4-nitro-1,2,5-oxadiazole)-1,2,4-oxadiazol-5(4H)-one (150 mg) was added. The reaction was warmed to room temperature to react for 3 hours, then diluted with ethyl acetate (20 ml), and the organic layer was washed with saturated brine, concentrated and column chromatography purified to provide 70 mg product, yield 30%.

$^1$HNMR (400 MHz, d6-DMSO): 8.09 (dd, 1H, J=2.0, 6.0 Hz), 7.72 (m, 1H), 7.60 (t, 1H, J=8.8 Hz), 6.54 (t, 1H, J=5.6 Hz), 6.43 (t, 1H, J=6.0 Hz), 3.38 (q, 2H, J=6.0 Hz), 3.14 (q, 2H, J=6.8 Hz), 2.86 (s, 3H), 0.84 (s, 9H), 0.02 (s, 3H), 0.00 (s, 3H).

Step 7: Synthesis of 4-((2-(methylsulfonyl)ethyl)amino)-N-(3-bromo-4-fluorophenyl)-N'-hydroxy-1,2,5-oxadioxazol-3-carboxamidine (LW105-1-1)

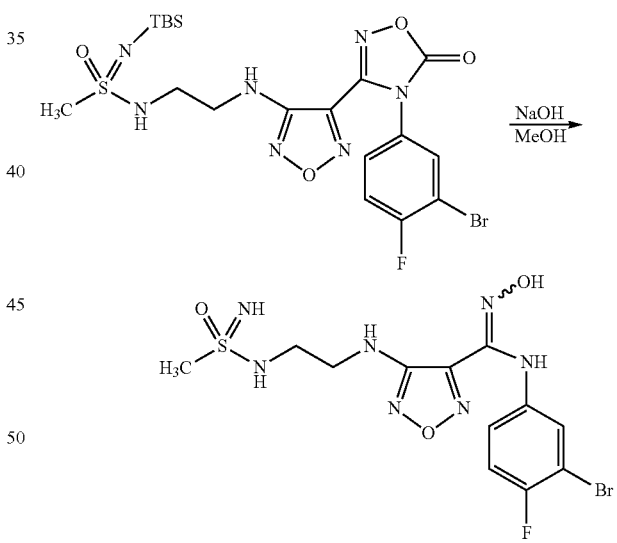

4-(3-Bromo-4-fluorophenyl)-3-(4-(2-(N'-tert-butyldimethylsilyl-methylsulfonylamino)ethyl)amino-1,2,5-oxadiazol)yl-1,2,4-oxadiazol-5(4H)-one (40 mg) was dissolved in methanol (5 ml), and 2N sodium hydroxide solution (0.44 ml) was added at room temperature. After stirred for an hour, the acetic acid was added to neutralize to pH=6-7. After concentration, the mixture was separated by a preparative chromatography plate to obtain 12 mg of solid, yield 39%.

$^1$HNMR (400 MHz, d6-DMSO): 11.49 (s, 1H), 8.88 (s, 1H), 7.19 (t, 1H, J=4.8 Hz), 7.12 (dd, 1H, J=2.4, 5.2 Hz), 6.77 (dd, 1H, J=2.0, 9.6 Hz), 6.28 (t, 1H, J=6.0 Hz), 3.33 (q, 2H, J=6.0 Hz), 3.15 (q, 2H, J=6.4 Hz), 2.86 (s, 3H).

MS (ESI): positive ion 436 (M+H)+, negative ion 434 (M−H)−.

Example 2

Chiral resolution of LW105-1-1 Preparative Liquid Chromatography was used for chiral resolution of racemic LW105-1-1.

Chiral column: Daicel AD column, 4.6*250 mm, 5 μm; flow rate 1.0 ml/min; detection wavelength: 220 nm; eluent (n-hexane:ethanol=65:35, volume ratio).

The compound 4-((2-(methylsulfonyl)ethyl)amino)-N-(3-bromo-4-fluorophenyl)-N'-hydroxy-1,2,5-oxadiazole-3-methylhydrazine was formulated into a 60 mg/ml ethanol solution, and the injection volume of each time was 2 ml. The peak with a retention time of 14.3 min was LW105-1-18 (20 mg), and the peak with a retention time of 21.1 min was LW105-1-19 (17 mg).

Example 3

4-((2-(methylsulfonyl)ethyl)amino)-N-(3-bromo-4-fluorophenyl)-N'-acetoxy-1,2,5-oxadiazole-3-carboxamidine

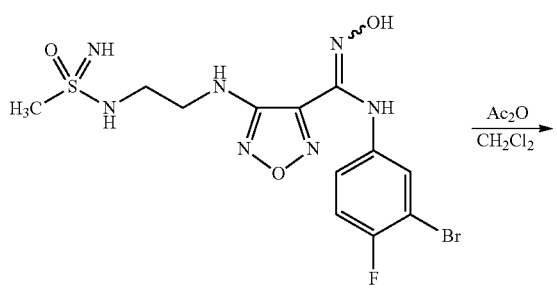

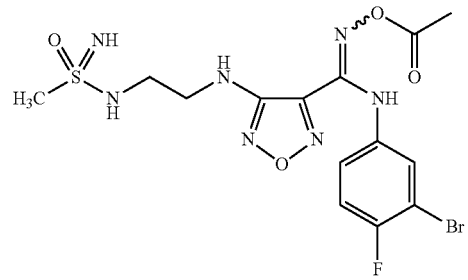

The compound 4-((2-(methylsulfonyl)ethyl)amino)-N-(3-bromo-4-fluorophenyl)-N'-hydroxy-1,2,5-oxadiazole-3-carboxamidine (50 mg) was dissolved in dichloromethane (2 ml), and triethylamine (0.1 ml) was added. The reaction was cooled to 0° C., and acetic anhydride (0.1 ml) was added, stirred for 30 min, washed with water. After dried and concentrated, the mixture was purified by column chromatography to provide 4-((2-(methylsulfonyl)ethyl)amino)-N-(3-bromo-4-fluorophenyl)-N'-acetoxy-1,2,5-oxadiazole-3-carboxamidine.

The compounds of the present application were synthesized using the preparation methods described herein (see table below).

| Number of Compound | Chemical structure | Analyze data NMR | MS |
|---|---|---|---|
| LW105-1-1 | 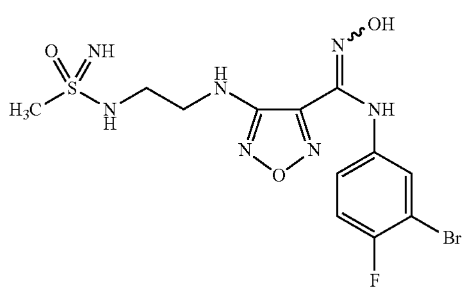 [SMILES: CS(=N)(=O)NCCNc1nonc1C(=NO)Nc1ccc(F)c(Br)c1] | 1HNMR(400 MHz, d6-DMSO): 11.49(s, 1H), 8.88(s, 1H), 7.19(t, 1H, J = 4.8 Hz), 7.12(dd, 1H, J = 2.4, 5.2 Hz), 6.77(dd, 1H, J = 2.0, 9.6 Hz), 6.28(t, 1H, J = 6.0 Hz), 3.33(q, 2H, J = 6.0 Hz), 3.15(q, 2H, J = 6.4 Hz), 2.86(s, 3H). | MS (ESI): positive ion 436 (M + H)+ Negative ion 434 (M − H)− |
| LW105-1-2 | 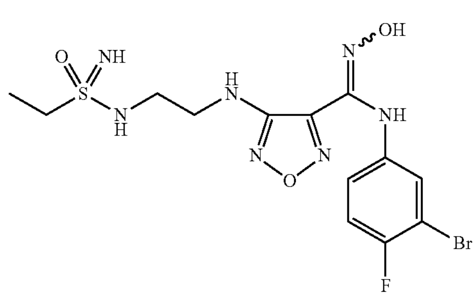 [SMILES: CCS(=N)(=O)NCCNc1nonc1C(=NO)Nc1ccc(F)c(Br)c1] | 1HNMR(400 MHz, d6-DMSO): 11.47(s, 1H), 8.85(s, 1H), 7.15(t, 1H, J = 8.8 Hz), 7.07(dd, 1H, J = 2.4, 5.6 Hz), 6.74(dd, 1H, J = 3.6, 8.8 Hz), 6.22(t, 1H, J = 5.6 Hz), 3.26(q, 2H, J = 6.0 Hz), 3.08(t, 2H, J = 6.0 Hz), 2.90(q, 2H, J = 7.2 Hz), 1.22(t, 3H, J = 7.2 Hz). | MS (ESI): positive ion 473 (M + H)+ Negative ion 448 (M − H)−, |

| Number of Compound | Chemical structure | Analyze data | |
|---|---|---|---|
| | | NMR | MS |
| LW105-1-3 | 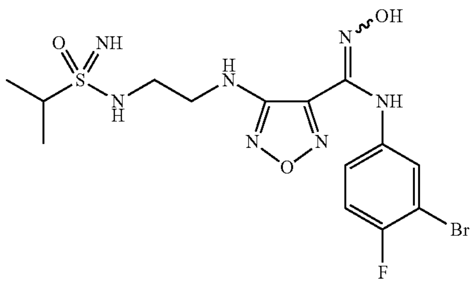 [SMILES: CC(C)S(=N)(=O)NCCNc1nonc1C(=NO)Nc1ccc(F)c(Br)c1] | ¹HNMR(400 MHz, d6-DMSO): 11.46(s, 1H), 8.85(s, 1H), 7.15(t, 1H, J = 8.8 Hz), 7.07(dd, 1H, J = 2.4, 5.6 Hz), 6.73(ddd, 1H, J = 3.6, 7.2, 9.2 Hz), 6.22(br, 1H), 3.26(q, 2H, J = 6.0 Hz), 3.10(t, 2H, J = 5.6 Hz), 3.02(m, 1H), 1.19(d, 3H, J = 6.0 Hz), 1.16(d, 3H, J = 6.0 Hz). | MS (ESI): positive ion 485 (M + Na)⁺ Negative ion 462 (M − H)⁻ |
| LW105-1-4 | 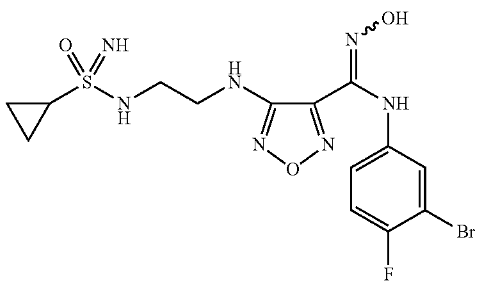 [SMILES: N=S(=O)(NCCNc1nonc1C(=NO)Nc1ccc(F)c(Br)c1)C1CC1] | ¹HNMR(400 MHz, d6-DMSO): 11.44(s, 1H), 8.84(s, 1H), 7.15(t, 1H, J = 8.4 Hz), 7.07(dd, 1H, J = 2.4, 6.0 Hz), 6.74(ddd, 6.23(t, 1H, J = 5.2 Hz), 3.27(t, 2H, J = 6.0 Hz), 3.13(t, 2H, J = 6.0 Hz), 2.44(m, 1H), 0.83(m, 4H). | MS (ESI): positive ion 464 (M + H)⁺ Negative ion 462 (M − H)⁻ |
| LW105-1-5 | 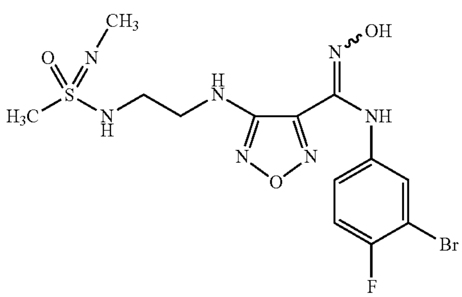 [SMILES: CN=S(C)(=O)NCCNc1nonc1C(=NO)Nc1ccc(F)c(Br)c1] | | MS (ESI): positive ion 450 (M + H)⁺ Negative ion 448 (M − H)⁻ |
| LW105-1-6 | 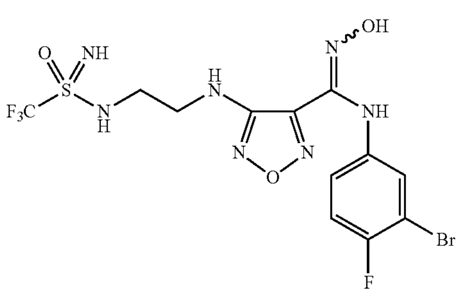 [SMILES: N=S(=O)(NCCNc1nonc1C(=NO)Nc1ccc(F)c(Br)c1)C(F)(F)F] | | MS (ESI): positive ion 490 (M + H)⁺ Negative ion 488 (M − H)⁻ |
| LW105-1-7 | 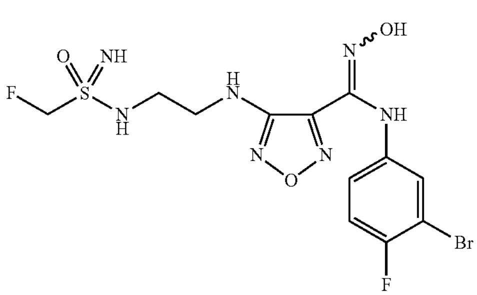 [SMILES: N=S(=O)(CF)NCCNc1nonc1C(=NO)Nc1ccc(F)c(Br)c1] | | MS (ESI): positive ion 454 (M + H)⁺ Negative ion 452 (M − H)⁻ |

-continued

| Number of Compound | Chemical structure | Analyze data | |
|---|---|---|---|
| | | NMR | MS |
| LW105-1-11 | 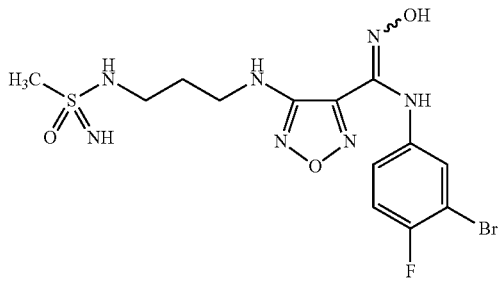 | $^1$HNMR(400 MHz, d6-DMSO): 11.54(s, 1H), 8.85(s, 1H), 7.15(t, 1H, J = 8.4 Hz), 7.07(dd, 1H, J = 2.4, 8.8 Hz), 6.73(dd, 1H, J = 3.2, 5.2 Hz), 6.28(t, 1H, J = 5.6 Hz), 3.23(q, 2H, J = 6.8 Hz), 2.95(t, 2H, J = 6.4 Hz), 2.82(s, 3H), 1.71(t, 2H, J = 6.8 Hz). | MS (ESI): positive ion 450 (M + H)$^+$ Negative ion 448 (M − H)$^-$ |
| LW105-1-12 | 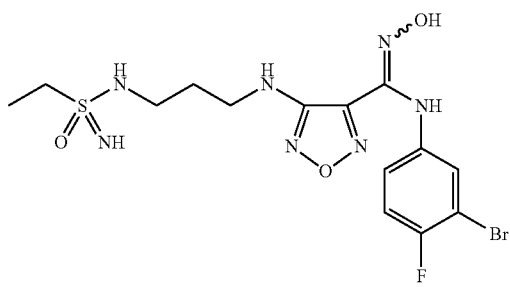 [SMILES: CCS(=N)(=O)NCCCNc1nonc1C(=NO)Nc1ccc(F)c(Br)c1] | $^1$HNMR(400 MHz, d6-DMSO): 11.55(s, 1H), 8.84(s, 1H), 7.15(t, 1H, J = 8.8 Hz), 7.06(dd, 1H, J = 2.0, 5.6 Hz), 6.73(m, 1H), 6.28(t, 1H, J = 5.6 Hz), 3.23(m, 2H), 2.92(m, 4H), 2.94(m, 2H), 1.70(m, 2H), 1.17 (t, 3H, J = 6.0 Hz). | MS (ESI): positive ion 450 (M + H)$^+$ Negative ion 462 (M − H)$^-$ |
| LW105-1-13 | 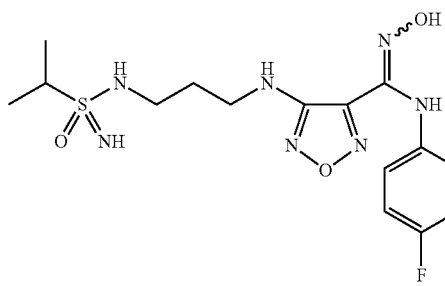 | $^1$HNMR(400 MHz, d6-DMSO): 11.52(s, 1H), 8.85(s, 1H), 7.15(t, 1H, J = 8.8 Hz), 7.06(dd, 1H, J = 2.0, 5.6 Hz), 6.73(m, 1H), 6.25(t, 1H, J = 5.6 Hz), 3.23(m, 2H), 3.02(t, 1H, J = 6.8 Hz), 2.94(m, 2H), 1.68(t, 2H, J = 6.4 Hz), 1.18(d, 3H, J = 6.0 Hz), 1.14(d, 3H, J = 6.0 Hz). | MS: ESI, positive ion: 477 (M + H)$^+$ Negative ion: 475 (M − H)$^-$ |
| LW105-1-14 | 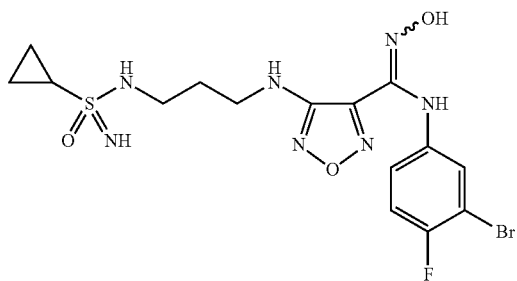 [SMILES: N=S(=O)(NCCCNc1nonc1C(=NO)Nc1ccc(F)c(Br)c1)C1CC1] | $^1$HNMR(400 MHz, d6-DMSO): 11.52(s, 1H), 8.83(s, 1H), 7.15(t, 1H, J = 8.8 Hz), 7.07(dd, 1H, J = 3.2, 5.2 Hz), 6.74(m, 1H), 6.29(t, 1H, J = 4.4 Hz), 3.26(m, 2H), 2.98(m, 2H), 2.42(m, 1H), 1.72(m, 2H), 0.82(m, 4H). | MS: ESI, positive ion: 476 (M + H)$^+$ Negative ion: 474 (M − H)$^-$ |
| LW105-1-15 | 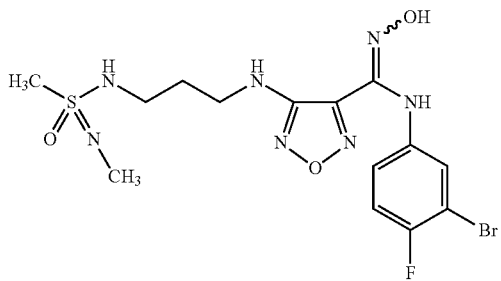 [SMILES: CN=S(C)(=O)NCCCNc1nonc1C(=NO)Nc1ccc(F)c(Br)c1] | | MS (ESI): positive ion 466 (M + H)$^+$ Negative ion 464 (M − H)$^-$ |

-continued

| Number of Compound | Chemical structure | NMR | MS |
|---|---|---|---|
| LW105-1-16 | (structure) | | MS (ESI): positive ion 504 (M + H)+ Negative ion 502 (M − H)− |
| LW105-1-17 | (structure) | | MS (ESI): positive ion 468 (M + H)+ Negative ion 466 (M − H)− |
| LW105-1-18 | (structure) or (structure) | ¹HNMR(400 MHz, d6-DMSO): 11.49(s, 1H), 8.88(s, 1H), 7.19(t, 1H, J = 4.8 Hz), 7.12(dd, 1H, J = 2.4, 5.2 Hz), 6.77(dd, 1H, J = 2.0, 9.6 Hz), 6.28(t, 1H, J = 6.0 Hz), 3.33(q, 2H, J = 6.0 Hz), 3.15(q, 2H, J = 6.4 Hz), 2.86(s, 3H). | MS (ESI): positive ion 436 (M + H)+ Negative ion 434 (M − H)− |
| LW105-1-19 | (structure) or | ¹HNMR(400 MHz, d6-DMSO): 11.49(s, 1H), 8.88(s, 1H), 7.19(t, 1H, J = 4.8 Hz), 7.12(dd, 1H, J = 2.4, 5.2 Hz), 6.77(dd, 1H, J = 2.0, 9.6 Hz), 6.28(t, 1H, J = 6.0 Hz), 3.33(q, 2H, J = 6.0 Hz), 3.15(q, 2H, J = 6.4 Hz), 2.86(s, 3H). | MS (ESI): positive ion 436 (M + H)+ Negative ion 434 (M − H)− |

| Number of Compound | Chemical structure | Analyze data | |
|---|---|---|---|
| | | NMR | MS |
| | 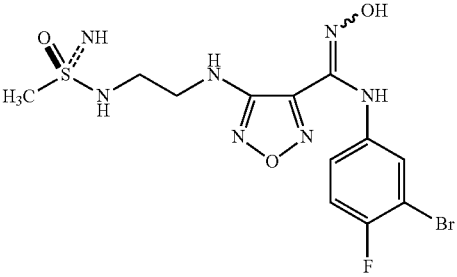 | | |

Example 4 Activity Test

1. IDO1 Enzyme Activity Test Method (NFK Green)

Content of research: the inhibitory effect of the compound on the activity of IDO1 enzyme was examined.

Materials and Methods

Reagents and Consumables

IDO assay kit (NTRC, Cat. No. NTRC-hTDO-1K), DMSO (Sigma, Cat. No. D2650), 384-well plate_compound dilution plate (Greiner, Cat. No. 781280), 384-well plate_test plate (Perkin Elmer, Cat. No. 6007299)

Experimental Method 10 nM IDO1 was incubated with compound or DMSO at 23° C. for 30 minutes, and L-type tryptophan was added at a final concentration of 100 uM and reacted for 1.5 hours. NFK green was added and incubated at 37° C. for 4 hours, and fluorescence signal data (excitation band, 400/25; emission band, 510/20) was corrected with Envision. Data analysis and mapping was conducted by XLfit5 software.

Final Test Concentration of Compounds:

The test compounds and the reference compound LW3018 were finally tested at concentrations ranging from 10 M to 0.51 nM, 3-fold gradient dilution, 10 concentrations, and two replicate wells.

Enzyme activity detection:

10 nM IDO1 was incubated with compound or DMSO at 23° C. for 30 minutes, and L-type tryptophan was added at a final concentration of 100 uM and reacted for 1.5 hours. NFK green was added and incubated at 37° C. for 4 hours, and fluorescence signal data (excitation band, 400/25; emission band, 510/20) was corrected with Envision. Data analysis and mapping was conducted by XLfit5 software.

2. IDO Cytology Test Method (LC-MS)

Content of research: the inhibitory effect of the compound on the activity of IDO1 in Hela cells was examined.

Materials and Methods

Reagents and Consumables

RPMI 1640 (phenol red free) medium (Invitrogen Cat. No. 11835030), fetal bovine serum (Invitrogen Cat. No. 10099141), penicillin and streptomycin (Invitrogen Gibco Cat. No. 15140-122), recombinant human interference γ (R&D system, Cat. No. 285-IF-100). 5% (w/v) trichloroacetic acid (Alfa Aesar Cat. No. A11156), DMSO (Sigma, Cat. No. D2650), 96-well plate_compound dilution plate (Axygen, Cat. No. WIPP02280), 96-well plate_test plate (Greiner, Cat. No. 655090)

Experimental Method

Final Test Concentration of Compounds:

The test compounds and the reference compound LW3018 were finally tested at concentrations ranging from 5 M to 0.76 nM, 3-fold gradient dilution, 9 concentrations, and two replicate wells.

Cytological Testing:

Hela cells were plated in 96-well cell culture plates at a number of 40,000 cells per well, and incubated with RPMI 1640 containing 10% fetal bovine serum for 5-6 hours. The diluted test compound and recombinant human interferon gammaa (final concentration at 100 ng/mL) were added to activate IDO1 expression. The cells were cultured in a 37° C. cell incubator which was enriched with 5% carbon dioxide for 20 hours, and the reaction was stopped with 5% trichloroacetic acid and incubated for 30 minutes at 50° C. After the cell culture solution was precipitated, the supernatant was sent to LC/MS to detect the content of kynurenine. Data analysis and mapping was conducted by XLfit5 software.

The test results of the IDO enzyme inhibitory activity and the cytostatic activity of the compound of the present application are shown in Table 1.

TABLE 1

IDO enzyme and cytostatic activity test results

| No. | IDO $IC_{50}$ (nM) | Hela $IC_{50}$ (nM) |
|---|---|---|
| LW105-1-1 | 22.3 | 11.5 |
| LW105-1-2 | 25.2 | 15.6 |
| LW105-1-3 | 19.4 | 12.7 |
| LW105-1-4 | 29.4 | 7.2 |
| LW105-1-11 | 26.5 | 11.1 |
| LW105-1-18 | 22.8 | 7.6 |
| LW105-1-19 | 22.3 | 6.7 |
| LW3018 (positive control) | 59.9 | 14.8 |

The above results indicate that the compounds of the present application (including racemates and enantiomers) have excellent inhibition against IDO enzymes and cells.

Example 5 In Vivo Efficacy Test of Mouse Colorectal Cancer CT26 Transplanted Tumor Under sterile conditions, CT26 cells in the proliferative phase were harvested, cell concentration was adjusted after digestion, and inoculated into the right hind limb of the mouse. Each mouse was inoculated with $1\times10^5$ CT26 cells in an inoculation volume of 0.1 mL. Four days after the inoculation, the average tumor volume was close to 20-30 mm³, and the mouse was administered in a randomized group. The day of administration was recorded as D0, and the negative control was given same amount of vehicle. Co-administration of LW 105-1-1 with Anti-CTLA4 antibody was also tested in this experiment. After the administration was started, the tumor long diameter and short diameter were measured 3 times per week. The experimental grouping and dosing schedule are shown in Table 2.

The preparation containing 5% DMA and 20% HPbCD aqueous solution as a solvent was administered by intravenous injection, and a preparation containing a solution comprising 5% DMA, 20% HPbCD and 0.1% CREMOPHOR EL as a solution was intragastrically administered. The animal strain was male C57BL/6 mice. Prior to the animal experiment, all animals were fasted and fed 4 hours after dosing; all animals were given free access to water.

TABLE 2

Animal experiment grouping and dosing schedule

| Group | N[1] | Compound therapy | Dosage (mg/kg) | Administration Route of administration | Administration frequency |
|---|---|---|---|---|---|
| 1 | 8 | Solvent control | — | oral | Twice a day, 2-3 |
| 2 | 8 | LW 105-1-1 | 30 mg/kg | oral | Twice a day, 2-3 weeks |
| 3 | 8 | LW 105-1-1 | 100 mg/kg | oral | Twice a day, 2-3 weeks |
| 4 | 8 | LW 105-1-1 | 300 mg/kg | oral | Twice a day, 2-3 weeks |
| 6 | 8 | CTLA-4 Ab | 10 mg/kg | intraperitoneal | Twice a week, 2-3 weeks |
| 7 | 8 | LW105-1-1 + CTLA-4 Ab | 300 + 10 mg/kg | Oral + intraperitoneal | Daily/twice a week, 2-3 weeks |

[1]Note: N: Number of mice per group;

The tumor inhibiting effect of the compound LW105-1-1 is shown in FIG. 1. The results showed that the compound LW105-1-1 of the present invention has a dose-dependent anti-tumor growth effect in a mouse CT26 tumor model of colorectal cancer. At 300 mg/kg dose, the tumor inhibition rate of LW105-1-1 was 40.6%, and the combination of LW105-1-1 and Anti-CTLA4 antibody showed a tumor inhibition rate of up to 96.4%.

Example 6 Study on the Pharmacokinetics of the Compound LW105-1-1 in Mice

1. Dosing Regimen 18 male C57BL/6 mice were intragastrically or intravenously administered with compound LW105-1-1 (Table 3).

TABLE 3

| Group | Compound | number of animal | Route of administration | Dosage (mg/kg) | Administrating volume (ml/kg) |
|---|---|---|---|---|---|
| 1 | LW105-1-1 | 6 | vein | 3 | 2 |
| 2 | LW105-1-1 | 6 | gavage | 30 | 10 |
| 3 | LW105-1-1 | 6 | gavage | 100 | 10 |

2. Blood Collection Time and Sample Preparation:

Intravenous administration group: before administration, 0.083, 0.25, 0.5, 1, 2, 4, 8 and 24 hours after.

Oral administration group: before administration, 0.25, 0.5, 1, 2, 4, 8 and 24 hours after 3. Sample Testing and Data Analysis:

Whole blood samples (0.03 mL) were collected from the saphenous vein at the indicated time (or other suitable blood collection sites), and all blood samples were added to a plastic centrifuge tube pre-filled with K2-EDTA anticoagulant and labeled. After the blood sample was collected, centrifuged for 10 minutes under 2 to 8° C. at 3000 g, and the supernatant plasma was aspirated, and quickly placed in dry ice, and kept at −20° C. or lower for LC-MS/MS analysis.

The concentrations of all samples were analyzed using LC-MS/MS. Plasma mean concentrations were processed using a non-compartmental model of WinNonlin™ Version 6.3 (Pharsight, Mountain View, Calif.) pharmacokinetic software, and pharmacokinetic parameters were calculated by linear logarithmic trapezoidal method.

4. Experimental Results:

The pharmacokinetic parameters of male C57BL/6 mice after intravenous administrating 3 mg/kg and oral gavage administrating 30 and 100 mg/kg are shown in Tables 4 and 5.

TABLE 4

Pharmacokinetic parameters of male C57BL/6 mice after intravenous administrating 3 mg/kg LW105-1-1

| dosage | $C_0$ (ng/mL) | $T_{1/2}$ (h) | $V_{dss}$ (L/kg) | Cl (mL/min/kg) | $AUC_{0\text{-}last}$ (ng·h/mL) | $AUC_{0\text{-}inf}$ (ng·h/mL) | $MRT_{0\text{-}last}$ (h) |
|---|---|---|---|---|---|---|---|
| 3 mg/kg | 2562 | 0688 | 1.87 | 34.5 | 1427 | 1451 | 0.904 |

TABLE 5

Pharmacokinetic parameters of male C57BL/6 mice after oral gavage administrating 30 and 100 mg/kg LW105-1-1

| dosage | C$_{max}$ (ng/mL) | T$_{max}$ (h) | T$_{1/2}$ (h) | AUC$_{0-last}$ (ng/mL·h) | AUC$_{0-inf}$ (ng/mL·h) | MRT$_{0-last}$ (h) | F% |
|---|---|---|---|---|---|---|---|
| 30 mg/kg | 4807 | 0.500 | 2.70 | 10129 | 10143 | 3.11 | 69.9 |
| 100 mg/kg | 20700 | 0.250 | 2.11 | 39342 | 39349 | 1.99 | 81.4 |

The results showed that after intravenous administration, the clearance rate (CL) of compound LW105-1-1 in mice was 34.5 mL/min/kg, and the steady-state volume (Vdss) was 1.87 L/kg, exposure quantity (AUC$_{0-last}$) was 1427 ng/mL h. After LW105-1-1 was gavage administrated at a dose of 100 mg/kg, the plasma peak time Tmax was 0.25 h and the exposure quantity (AUC$_{0-last}$) was 39,432 ng/mL h. After dose standardization, the absolute bioavailability was 81.4%.

All literatures mentioned in the application application are incorporated herein by reference, as though each one is individually incorporated by reference. Additionally, it should be understood that after reading the above teachings, those skilled in the art can make various changes and modifications to the present application. These equivalents also fall within the scope defined by the appended claims.

The invention claimed is:

1. A compound of formula I, or a pharmaceutically acceptable salt thereof, a deuterated compound, a stereoisomer or a tautomer thereof:

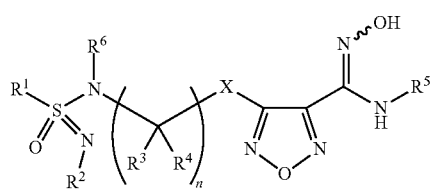

(I)

wherein, $R^1$ is $C_1$-$C_{10}$ alkyl substituted by one or more substituents selected from the group consisting of halogen, hydroxy, —NH$_2$, nitro, —CN, $C_1$-$C_4$ haloalkyl, $C_1$-$C_4$ alkoxy, $C_3$-$C_6$ cycloalkyl, $C_2$-$C_4$ alkenyl, $C_2$-$C_4$ alkynyl, phenyl, and benzyl, or $R^1$ is substituted or unsubstituted $C_3$-$C_{10}$ cycloalkyl, substituted or unsubstituted $C_2$-$C_{10}$ alkenyl, substituted or unsubstituted $C_3$-$C_{10}$ alkynyl, substituted or unsubstituted $C_6$-$C_{20}$ aryl, or substituted or unsubstituted $C_3$-$C_{14}$ heteroaryl;

$R^2$, $R^3$, and $R^4$ are each independently hydrogen, substituted or unsubstituted $C_1$-$C_{10}$ alkyl, substituted or unsubstituted $C_3$-$C_{10}$ cycloalkyl, substituted or unsubstituted $C_2$-$C_{10}$ alkenyl, substituted or unsubstituted $C_3$-$C_{10}$ alkynyl, substituted or unsubstituted $C_6$-$C_{20}$ aryl, or substituted or unsubstituted $C_3$-$C_{14}$ heteroaryl; le and $R^2$, le and $R^3$, or $R^3$ and $R^4$ may together form a three to eight membered carbocyclic ring or a three to eight membered heterocyclic ring, wherein the hetero atom may be sulfur, oxygen, or nitrogen, and if the heterocyclic ring has a nitrogen atom, the nitrogen atom may be optionally substituted by $C_1$-$C_6$ alkyl or $C_3$-$C_6$ cycloalkyl;

$R^5$ is $C_6$-$C_{20}$ aryl, or five- or six-membered heteroaryl; $R^5$ may be substituted by one or more groups selected from the group consisting of halogen, $C_1$-$C_6$ alkyl, $C_1$-$C_6$ alkoxy, hydroxyl, amino, nitro, aldehyde, —CF$_3$, —CN, —SF$_5$, NR$^a$R$^b$, carboxyl, —COR$^a$, —CO$_2$C$_1$-C$_6$ alkyl, —CONR$^a$R$^b$ —S(O)R$^a$, —S(O)$_2$R$^a$, —S(O)(NH)R$^a$, —S(O)(NR$^d$)R$^a$, —S(O)$_2$NR$^a$R$^b$, —P(O)Me$_2$, and —P(O)(OMe)$_2$; wherein each R$^a$ and each R$^b$ are independently hydrogen, substituted or unsubstituted $C_1$-$C_{10}$ alkyl, substituted or unsubstituted $C_3$-$C_{10}$ cycloalkyl, substituted or unsubstituted $C_2$-$C_{10}$ alkenyl, substituted or unsubstituted $C_6$-$C_{20}$ aryl, or substituted or unsubstituted $C_3$-$C_{14}$ heteroaryl; R$^a$ and R$^b$ may together form a three to eight membered or four to eight membered heterocyclic ring, wherein the hetero atom may be sulfur, oxygen, or nitrogen, and if there is nitrogen atom on the heterocyclic ring, the nitrogen atom is optionally substituted by $C_1$-$C_6$ alkyl or $C_3$-$C_6$ cycloalkyl;

$R^6$ is hydrogen;

X is a single bond, O, S or NH, or NR$^d$;

$R^d$ is selected from the group consisting of $C_1$-$C_{10}$ alkyl, $C_3$-$C_{10}$ cycloalkyl, $C_6$-$C_{20}$ aryl, and $C_3$-$C_{14}$ heteroaryl;

n is an integer from 2 to 8; and the term "substituted" means that the group has one or more substituents selected from the group consisting of halogen, hydroxy, —NH$_2$, nitro, —CN, $C_1$-$C_4$ alkyl, $C_1$-$C_4$ haloalkyl, $C_1$-$C_4$ alkoxy, $C_3$-$C_6$ cycloalkyl, $C_2$-$C_4$ alkenyl, $C_2$-$C_4$ alkynyl, phenyl, and benzyl.

2. The compound of claim 1 or a pharmaceutically acceptable salt thereof, a deuterated compound thereof, a stereoisomer thereof or a tautomer thereof, wherein the compound is as shown in formula (II),

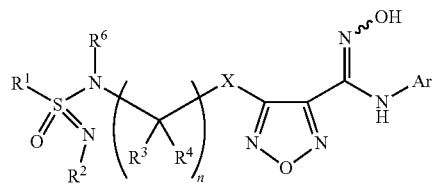

(II)

wherein,

Ar is benzene ring, and Ar may be substituted by one or more groups selected from the group consisting of halogen, $C_1$-$C_6$ alkyl, $C_1$-$C_6$ alkoxy, hydroxy, amino, nitro, aldehyde, —CF$_3$, —CN, —SF$_3$, —SF$_5$, NR$^a$R$^b$, carboxyl group, —COR$^a$, —CO$_2$C$_1$-C$_6$ alkyl, —CONR$^a$R$^b$, —S(O)R$^a$, —S(O)$_2$R$^a$, —S(O)(NH)R$^a$, —S(O)(NR$^d$)R$^a$, —S(O)$_2$NR$^a$R$^b$;

R$^a$, R$^b$, R$^d$, R$^3$, R$^4$, R$^6$, R$^2$, R$^1$, and X are as defined above;

n is an integer from 2 to 6.

3. The compound according to claim 2, or a pharmaceutically acceptable salt thereof, a deuterated compound thereof, a stereoisomer thereof or a tautomer thereof, wherein in the formula (II), Ar is a benzene ring substituted by one or two groups selected from the group consisting of halogen, hydroxy, amino, nitro, —$CF_3$ and —CN;

$R^1$ is $C_1$-$C_6$ alkyl substituted by one or more halogens or $R^1$ is $C_3$-$C_6$ cycloalkyl, $C_6$-$C_{10}$ aryl, or $C_3$-$C_8$ heteroaryl containing at least one hetero atom, each of which is unsubstituted or substituted by one or more halogens; and $R^2$ is hydrogen or $C_1$-$C_6$ alkyl, or $R^1$ and $R^2$ may together form a three to eight membered carbocyclic ring or a three to eight membered heterocyclic ring;

the hetero atom as defined above is selected from the group consisting of sulfur, oxygen and nitrogen; if the hetero ring comprises a nitrogen atom, the nitrogen atom is optionally substituted by $C_1$-$C_6$ alkyl or $C_3$-$C_6$ cycloalkyl;

$R^3$ and $R^4$ are each independently hydrogen or $C_1$-$C_6$ alkyl;

n is 2 or 3;

X is NH or $NR^d$; and $R^d$ is $C_1$-$C_6$ alkyl.

4. The compound according to claim 3, or a pharmaceutically acceptable salt thereof, a deuterated compound thereof, a stereoisomer thereof or a tautomer thereof, wherein in the formula (II), Ar is benzene ring which is substituted by two halogen atoms;

$R^1$ is $C_3$-$C_6$ cycloalkyl;

$R^2$ is hydrogen;

$R^3$ and $R^4$ are each independently hydrogen;

n is 2 or 3;

X is NH.

5. The compound according to claim 4, or a pharmaceutically acceptable salt thereof, a deuterated compound thereof, a stereoisomer thereof or a tautomer thereof, wherein in the formula (II), $R^1$ is cyclopropyl;

$R^2$ is hydrogen;

$R^3$ and $R^4$ are each independently hydrogen;

n is 2 or 3;

X is NH;

Ar is benzene ring which is substituted by two halogen atoms at the para and meta positions.

6. The compound according to claim 3, or a pharmaceutically acceptable salt thereof, a deuterated compound thereof, a stereoisomer thereof or a tautomer thereof, wherein in the formula (II), $R^1$ selected from the group consisting of cyclopropyl, $CH_2F$, $CHF_2$, $CF_3$, $CH_2Cl$, $CHCl_2$, $CCl_3$, $CHFCH_3$, $CF_2CH_3$, $CHFCH_2F$, $CF_2CH_2F$, $CHFCHF_2$, $CF_2CHF_2$, $CHFCF_3$ or $CF_2CF_3$;

Ar is benzene ring, of which the para position is substituted by F, and the meta position is substituted by Br.

7. The compound of claim 1 or a pharmaceutically acceptable salt thereof, a deuterated compound thereof, a stereoisomer thereof or a tautomer thereof, wherein the compound is selected from the following compounds:

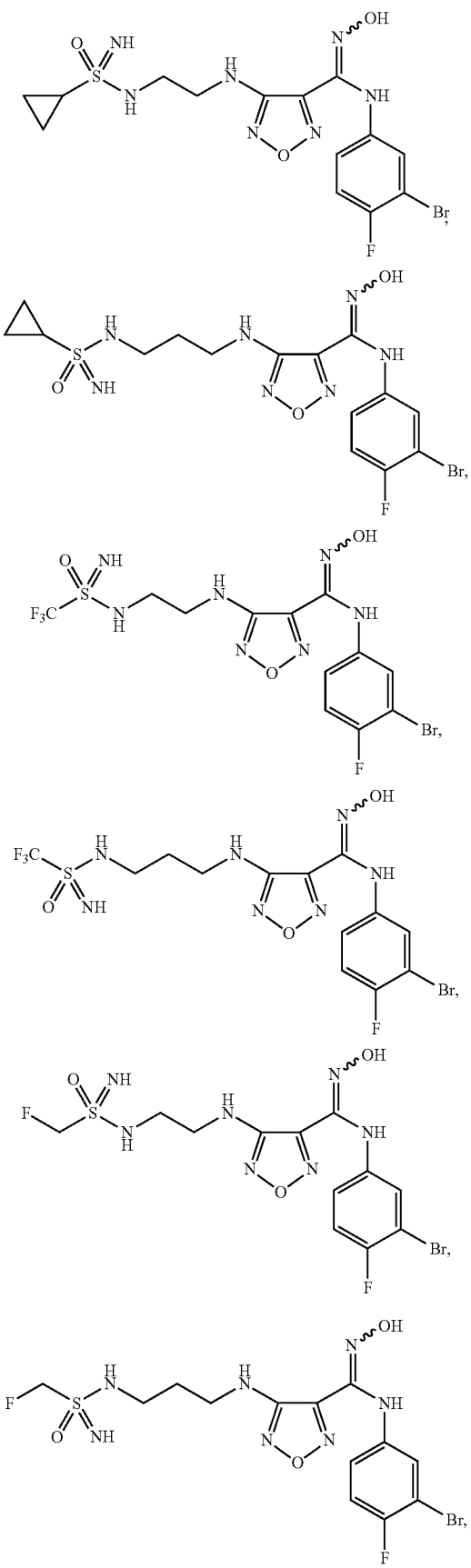

-continued

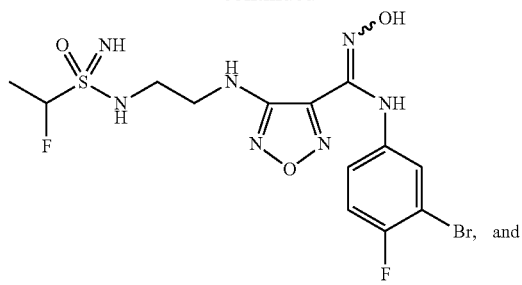

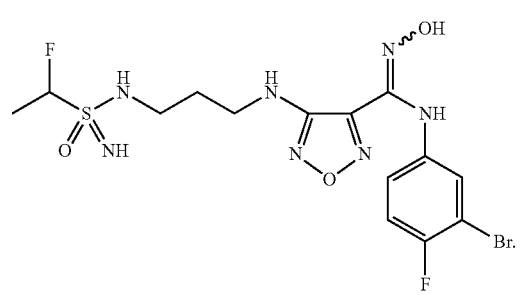

8. A method for the preparation of a compound according to claim 1, comprising the steps:

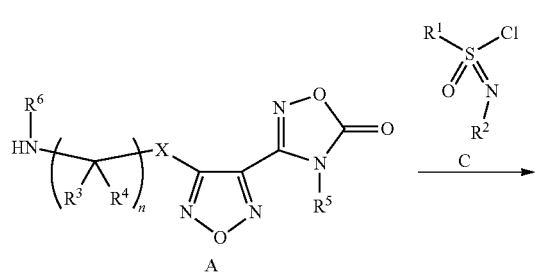

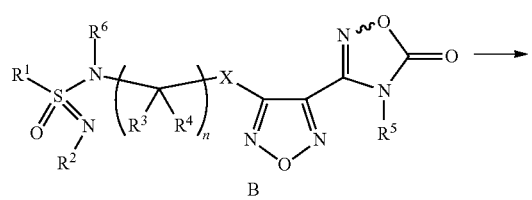

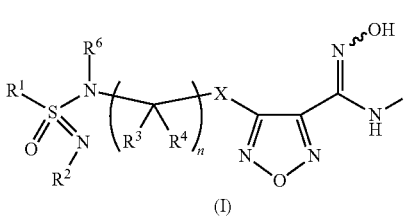

(a) reacting compound A with compound C to give compound B;
(b) ring-opening compound B under alkaline hydrolysis conditions to give the final product of formula I;
in each formula, $R^1$, $R^2$, $R^3$, $R^4$, $R^5$, $R^6$, and n are as defined above.

9. A method for the preparation of a compound according to claim 1, comprising the steps:

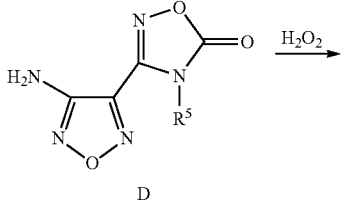

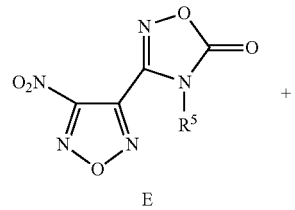

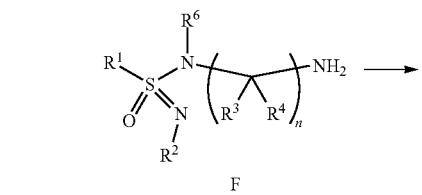

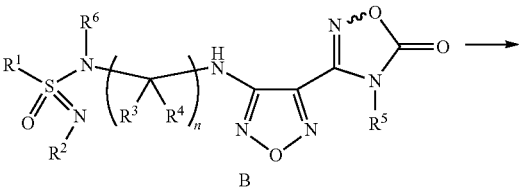

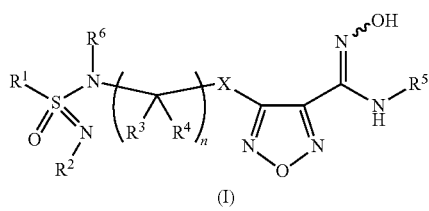

(a) under the catalysis of sulfuric acid, oxidizing compound D by hydrogen peroxide to provide compound E;
(b) Compound E and compound F undergo a substitution reaction to obtain compound B;
(c) ring-opening compound B under alkaline hydrolysis conditions to give the final product of formula I;
in each formula, $R^1$, $R^2$, $R^3$, $R^4$, $R^5$, $R^6$, and n are as defined above.

10. A method for treating an indoleamine-2,3-dioxygenase mediated disease, comprising:
administering a compound according to claim 1, a pharmaceutically acceptable salt thereof, a deuterated compound thereof, a stereoisomer thereof or a tautomer thereof, to a subject in need thereof, wherein the indoleamine-2,3-dioxygenase mediated disease is selected from the group consisting of cancer, a neurodegenerative disease, an eye disease, a psychological disorder, depression, anxiety, Alzheimer's disease, and an autoimmune disease; and the cancer is selected from the group consisting of colorectal cancer, breast cancer, gastric cancer, lung cancer, colon cancer, pancreatic cancer, ovarian cancer, prostate cancer, kidney cancer, liver cancer, brain cancer, Melanoma, multiple myeloma, chronic myeloid leukemia, hematological tumors, and metastatic lesions of tissues or organs away from the primary site of the tumor.

11. A pharmaceutical composition, wherein the pharmaceutical composition comprises the compound of claim 1, or a pharmaceutically acceptable salt thereof, a deuterated compound thereof, a stereoisomer thereof, or a tautomer thereof, and pharmaceutically acceptable carriers.

12. A pharmaceutical composition, wherein the pharmaceutical composition comprises the compound of claim 1, or a pharmaceutically acceptable salt thereof, a deuterated compound thereof, a stereoisomer thereof, or a tautomer thereof, and one or more anti-tumor medicines.

13. The pharmaceutical composition according to claim 12, wherein the antitumor drug is selected from the group consisting of PD-1 antibodies, CTLA-4 antibodies, PD-L1 antibodies, and PD-L2 antibodies.

14. A compound, selected from the group consisting of:

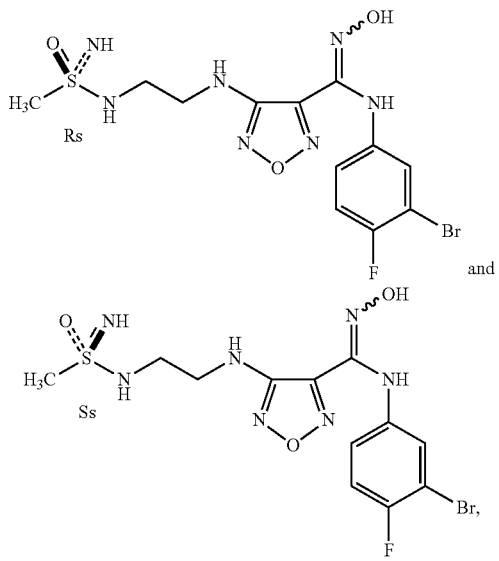

or a pharmaceutically acceptable salt thereof, a deuterated compound thereof, or a tautomer thereof.

15. A pharmaceutical composition, wherein the pharmaceutical composition comprises the compound of claim 14, or a pharmaceutically acceptable salt thereof, a deuterated compound thereof, or a tautomer thereof, and pharmaceutically acceptable carriers.

* * * * *